United States Patent [19]

Krueger et al.

[11] Patent Number: 5,075,288
[45] Date of Patent: Dec. 24, 1991

[54] SOMNOGENIC FRAGMENT OF INTERLEUKIN-1 BETA

[75] Inventors: James M. Krueger, Germantown, Tenn.; Ferenc Obal, Jr., Szeged, Hungary; Arnold E. Postlethwaite, Eads; Jerome M. Seyer, Memphis, both of Tenn.

[73] Assignee: The University of Tennessee Research Corporation, Knoxville, Tenn.

[21] Appl. No.: 577,920

[22] Filed: Sep. 5, 1990

[51] Int. Cl.$^5$ ............... A61K 37/02; A61K 37/18; C07K 7/04; C07K 13/00
[52] U.S. Cl. ............... 514/12; 530/324; 530/351
[58] Field of Search ............... 514/12; 530/324, 351

[56] References Cited

U.S. PATENT DOCUMENTS

| | | | |
|---|---|---|---|
| 2,575,763 | 11/1951 | Menkin | 424/537 |
| 4,116,949 | 9/1978 | Goodman et al. | 525/54.1 |
| 4,537,878 | 8/1985 | Plotnikoff | 514/2 |
| 4,668,661 | 5/1987 | Karnovsky et al. | 514/8 |
| 4,762,914 | 8/1988 | Auron et al. | 530/351 |
| 4,766,069 | 8/1988 | Auron et al. | 435/70 |
| 4,801,686 | 1/1989 | Kronheim | 530/351 |
| 4,808,611 | 2/1989 | Cosman | 514/12 |
| 4,902,505 | 2/1990 | Pardridge et al. | 424/85 |
| 4,935,343 | 6/1990 | Allison et al. | 435/7 |
| 4,994,553 | 2/1991 | Schmidt et al. | 530/327 |

OTHER PUBLICATIONS

M. Opp, *American Journal of Physiology* 257: R528-R535, 1989.

*Primary Examiner*—Jeffrey E. Russel
*Assistant Examiner*—Stephen Walsh
*Attorney, Agent, or Firm*—Leudeka, Hodges, Neely & Graham

[57] ABSTRACT

A protein fragment for inducing sleep in mammals comprising a fragment of interleukin-1 $\beta$ from about amino acid 208 to about amino acid 240 and its physiologically active derivatives. The fragment comprises the amino acids sequence:

Lys—Lys—Lys—Met—Glu—Lys—Arg—Phe—Val—
-210

Phe—Asn—Lys—Ile—Glu—Ile—Asn—Asn—Lys—
-220

Leu—Glu—Phe—Glu—Ser—Ala—Gln—Phe—Pro—
-230

Asn—Trp—Tyr—Ile—Ser—Thr.
-240

The protein fragment may be derived by synthetic methods and a cysteine residue may be attached to the last threonine residue.

10 Claims, No Drawings

SOMNOGENIC FRAGMENT OF INTERLEUKIN-1 BETA

The present invention was developed, in part, with funds from the National Institutes of Health, the Veteran's Administration, the Office of Naval Research, and the U.S. Army Medical Research and Development Command. The United States Government has certain rights in the present invention.

Interleukin-1 (IL1) refers to a group of cytokines that possess similar biological activities and which are derived by posttranslational processing from two distinct gene products, IL1α and IL1β. These gene products are synthesized as precursors with a molecular weight of about 33 kd and can be directly secreted or enzymatically processed into various forms of lower molecular weight.

IL1β has many nervous system activities including activation of certain facets of the acute phase response, induction of fever, and enhancement of non-rapid-eye-movement sleep (NREMS) in mammals. The anterior hypothalamus-preoptic area of the brain is involved in these IL1-induced responses and there are IL1β-immunoreactive neurons in the human hypothalmus. In addition, IL1β-mRNA and IL1 receptors have been found in the normal rat brain, including the hypothalamus.

There have been several attempts to define the structural requirements for IL1 activities by testing synthetic fragments of IL1 in various biological assay systems. To date, no IL1 fragments have been shown effective in inducing NREM sleep.

It is an object of the present invention to provide a protein fragment which will induce NREM sleep in a manner that is similar to the induction of NREM sleep in mammals induced by the whole protein IL1β.

The present invention provides for a protein fragment for inducing sleep in mammals comprising a fragment of interleukin-1β from about amino acid 208 to about amino acid 240 and its physiologically active derivatives. The protein fragment comprises the amino acid sequence:

```
Lys—Lys—Lys—Met—Glu—Lys—Arg—Phe—Val—
                                    -210
Phe—Asn—Lys—Ile—Glu—Ile—Asn—Asn—Lys—
                                -220
Leu—Glu—Phe—Glu—Ser—Ala—Gln—Phe—Pro—
                            -230
Asn—Trp—Tyr—Ile—Ser—Thr,
                      -240,
``` and its physiologically active derivatives. It is well known to those skilled in the art that certain derivatives of protein fragments will retain their biological activity. For example, it is expected that the substitution of D amino acid for L amino acid in the fragments of the present invention would result in a protein fragment having a sleep-inducing action. For example, L-tyr could be replaced by D-tyr. Such changes are often useful to reduce the rate of peptide breakdown, thereby reducing the amount needed for an effective somnogenic dose. By way of example, it has been reported that similar changes were made in the nonapeptide DSIP, and that it retained its somnogenic activity (Kovalzon, V. et al., *Pharmacol. Biochem. Behav.*, 24:889-894 (1986)).

It is also expected that phosphorylation of certain amino acid residues in the protein fragments of the present invention would result in sleep-inducing peptides. For example, if a ser residue is phosphorylated, it is anticipated that such analog would be somnogenic. By way of example, phosphorylation of the ser residue of DSIP results in a molecule that retains its ability to induce sleep (Oral Communication by S. Inoye (Tokyo) at the Endogenous Sleep Factors Seminar, Nov. 11, 1988, Honolulu, Hi.).

The protein fragment is derived by synthetic methods. The fragment may further comprise a cysteine residue attached to the last threonine residue.

The present invention also provides a method for inducing sleep in mammals comprising administering a physiologically effective amount of the fragments described above. The physiologically effective amount of the fragment can be between about 5 μg and about 25 μg per kg body weight.

The present invention further provides for a pharmaceutical composition for inducing sleep in mammals. The composition comprises a physiologically acceptable carrier and the protein fragments described above.

The protein fragment of the present invention can be administered to mammals orally, rectally, intravenously (IV), intramuscularly (IM), interperitoneally (IP) or intraventricularly (ICV) in the form of a composition containing the active agent in combination with any non-toxic physiologically acceptable carrier, many of which are well known in the art. As desired, an antipyretic may be added. The exact dosage form and size of dose depend upon body size and case history of the individual. In general, an amount of active agent from 5 μg to 25 μg per kg body weight is sufficient to induce NREM sleep when injected ICV.

The IL1β fragment enhanced NREM sleep, EEG slow-wave amplitudes and $T_{br}$ after the injection of approximately 25 μg. The time courses of the effects were similar to those after the injection of recombinant human IL1β (hu-rIL1β). The dose of protein fragment 208-240 reduced REM sleep but this effect was not significant. There was no appearance of abnormal behavior due to the injection of the protein fragment.

In order to facilitate a further understanding of the invention the following example is given primarily for the purposes of illustrating certain more specific details thereof.

EXAMPLE

Compounds Tested

Recombinant human IL1β (hu-rIL1β) was prepared by Cistron Biotechnology, Incorporated of Pinebrook, N.J. IL1β fragments of amino acids 178-207 199-225, and 208-240 were synthesized using known techniques. The sequences of those fragments are shown in Table 1.

TABLE 1

Amino Acid Sequences of IL1β Fragments

```
117-134  Ala—Pro—Val—Arg—Ser—Leu—Asn—Cys—
                                    -120
         Thr—Leu—Arg—Asp—Ser—Glu—Glu—Lys—
                                        -130
         Ser—Leu
```

TABLE 1-continued
Amino Acid Sequences of IL1β Fragments

| | |
|---|---|
| 178-207 | Leu—Lys—Glu—Lys—Asn—Leu—Tyr—Leu—-180 |
| | Ser—Cys—Val—Leu—Lys—Asp—Asp—Lys—-190 |
| | Pro—Thr—Leu—Gln—Leu—Glu—Ser—Val—-200 |
| | Asp—Pro—Lys—Asn—Tyr—Pro |
| 199-228 | Glu—Ser—Val—Asp—Pro—Lys—Asn—Tyr— |
| | Pro—Lys—Lys—Met—Glu—Lys—Arg—Phe—-210 |
| | Val—Phe—Asn—Lys—Ile—Glu—Ile—Asn—-220 |
| | Lys—Glu—Phe |
| 208-240 | Lys—Lys—Lys—Met—Glu—Lys—Arg—Phe—-210 |
| | Val—Phe—Asn—Lys—Ile—Glu—Ile—Asn—-220 |
| | Asn—Lys—Leu—Glu—Phe—Glu—Ser—Ala—-230 |
| | Gln—Phe—Pro—Asn—Trp—Tyr—Ile—Ser—Thr-240 |
| 247-269 | Pro—Val—Phe—Leu—Gly—Gly—Thr—Lys—-250 |
| | Gly—Gly—Gln—Asp—Ile—Thr—Asp—Phe—-260 |
| | Thr—Met—Gln—Phe—Val—Ser—Ser |

Animals

A lateral cerebral ventricular guide cannula, a thermistor, and stainless steel screw electroencephalographic (EEG) electrodes were surgically implanted into male, New Zealand white pasteurella-free rabbits (about 3.5 kg). EEG electrodes were placed over the frontal and parietal cortices A 50,000 ohm calibrated thermistor (Model 4018, Omega Engineering, Stamford, Conn.) was implanted over the parietal cortex to measure brain temperature ($T_{br}$). Insulated leads from the screws and the thermistor were routed to an amphenol plug attached to the skull with dental acrylic (DUZ-ALL, Coralite Dental Products, Skokie, Ill.). The guide cannula was placed in the left lateral cerebral ventricle. A minimum of two weeks was allowed for recovery before the animals were habituated to the recording chambers (Hotpack 352600, Philadelphia, Pa.). Food and water were available ad libitum.

Apparatus and Recording

Each recording chamber contained an electronic swivel (Stoelting, Chicago, Ill.) suspended by a shock-absorbing system. A flexible tether connected the swivel to the Amphenol connector on the rabbit's head, thus allowing freedom of movement. An accelerometer (Grass, SPAI, Quincy, Mass.) attached to the shock-absorbing system provided an indication of body movement. The cables from the swivel and the accelerometer were connected to Grass 7D polygraphs in an adjacent room. The polygraphs recorded EEG, $T_{br}$, and body movement for each animal. The EEG for each rabbit was passed through band-pass filters with the 0.5-3.5 Hz (delta), 4.0-7.5 Hz (theta), 8.0-12.5 Hz (alpha), and 13.0-15.0 Hz (beta) frequency bands rectified and averaged for 1-min intervals by a Buxco model 24/32 data logger (Buxco Electronics, Sharon, Conn.). These values for 1-min periods were used to compute hourly averages. EEG amplitudes in the delta frequency band during 1-min epochs of NREMS for each of the six postinjection hours were also determined. The 10 samples of greatest magnitude in each hour were averaged for each rabbit during control and test NREM sleep periods. In addition, the ratio of theta to delta activity was also computed and displayed on the polygraph simultaneously with the EEG, $T_{br}$, and body movement to facilitate scoring of vigilance states. $T_{br}$S were also recorded using a data logger (Acrosystems 400, Beverly, Mass.), with values for each rabbit sampled at 10-min intervals. NREM sleep and REM sleep were measured as a percent of time over a six-hour recording period. Colonic temperatures ($T_{co}$) were taken with a flexible thermistor (YSI, Inc., Yellow Springs, Ohio) at the time of injection and at the end of 6-h recording session.

Experimental protocol

IL1 fragments were dissolved in appropriate volumes of artificial cerebrospinal fluid (aCSF) (2 mM KCl, 1.15 mM $CaCl_2$, and 0.96 mM $MgCl_2$ in pyrogen free saline, 1.55 mM NaCl [Abbott, N. Chicago, Ill.] Hu-rIL1β was supplied in phosphate-buffered saline (PBS) (0.4 mg/ml). All substances were injected into a lateral cerebral ventricle (ICV). Injection volumes were 12-25 μl per rabbit; each injection lasted about 2 min. Animals were injected between 0900 and 1000 h. Control recordings were obtained from each animal after injection of vehicle (aCSF). After injections, animals were recorded from the next 6 h.

$PGE_2$ production by rheumatoid arthritis synovial cells

Synovial tissue obtained at surgery from patients with rheumatoid arthritis (RA) undergoing joint replacement was cut into pieces of 2 mm or less and incubated at approximately 100 mg/ml in serum-free minimal essential medium (MEM) containing 1 mg/ml bacterial collagenase (Sigma Chemical Co., St. Louis, Mo.) and 10 μg/ml testicular hyaluronidase (Sigma) at 37° C. with rocking. After 3-4 h, the suspension was centrifuged at 150 xg for 10 min. The cells were resuspended ($10^5$ cells/ml) in MEM containing 20% fetal calf serum (FCS) and plated in 100-mm diameter Petri dishes (10 ml per dish). The disaggregated cells were cultured overnight at 37° C. in 5% $CO_2$, and the nonadherent cells were aspirated off by vigorous pipetting. Adherent synovial cells were maintained in culture with medium change every four days until they reached confluency, at which time they were subcultured after trypsinization and grown in maintenance medium (Eagle's MEM Supplemented with nonessential amino acids, ascorbic acid, amphotericin B (1 μg/ml), $NaHCO_3$, penicillin (100 U/ml), and streptomycin (100 μ/ml), FCS (9%), and PBS).

Adherent rheumatoid synovial cells (ARSC) were set up in 24-well number 3424 Costar plates (Cambridge, Mass.) by adding $5 \times 10^4$ cells per well in 0.5 ml of maintenance medium. After 72 h, the monolayers were confluent, and medium was changed to serum-free maintenance medium for 24 h. Medium was changed, and to each well was added 450 μl serum-free maintenance medium and 50 μl PBS or 50 μl PBS containing various concentrations of synthetic IL1 peptides, previously sterilized by micropore filtration. After 24 h, culture supernatants were harvested, and $PGE_2$ was extracted from the supernatants and quantitated by radioimmunoassay.

T cell proliferation assays

Thymus glands were removed from 6-10 week old CD1 mice after mice had been sacrificed by cervical dislocation. Thymocytes were isolated by gently homogenizing the thymus glands in a dounce homogenizer. Thymocytes were suspended in RPMI 1640 containing 7.5% FCS and $5 \times 10^{-6}$ M 2-mercaptoethanol. Aliquots of the cell suspension (100 μl) were dispensed into wells of flat bottom microtiter plates (Linbro Plastics), and samples (50 μl) suspended in RPMI 1640 were added to appropriate wells. Plates were incubated at 37° C., 5% $CO_2$, in a humidified atmosphere for 60 h, and wells were pulsed with [$^3$H] thymidine (1 μCi, 1.9 Ci/mol) for 12h. After the 12-h pulse, cells were harvested onto paper filter pads with a multiple-sample harvester, and thymocyte proliferation was determined by scintillation counting. In some experiments, the murine T cell line D10 was used instead of thymocytes as target cells using phytohemmagglutinin (1 μg/ml) as costimulant.

Statistical analysis

Data from all experiments were analyzed with the SPSS$^{x}$ Information System. Friedman's test for k-related samples was used to test for differences across the 6-h recording periods. If significant differences were indicated, the Wilcoxon matched-pairs signed-ranks test was used to identify the specific hours in which the differences occurred. An alpha level of $P < 0.05$ was accepted as indicating significance.

Several synthetic fragments of IL1β were tested for somnogenic and pyrogenic activity. IL1β peptides 117-134, 178-207, 199-228, and 247-269 failed to alter sleep or $T_{br}$. Peptides 178-207, 199-228, and 247-269 stimulated T cell proliferation, as is shown in Table 2. In contrast to the results obtained with the other fragments, IL1β peptide 208-240 enhanced NREM sleep, EEG slow-wave amplitudes, and $T_{br}$ after ICV injection of 25 μg as shown in Table 3. The time courses of these events were similar to those observed after injection of hu-rIL1β. This dose of peptide 208-240 also reduced REM sleep, but these effects were not significant. Peptide 208-240 did not appear to induce abnormal behavior. Further, peptide 208-240, although not mitogenic for T cells, stimulated $PGE_2$ production by ARSC (Table 2).

From Table 2, it may be seen that IL1 β fragment 208-240 stimulates the production of PGE without the proliferation of T cells as shown by the other fragments. From Table 3, it is seen that fragment 208-240 increases NREM sleep and increases colonic temperature in a manner similar to the effects of the whole protein, IL1β. This is in contrast to the other fragments which show no significant change in NREM sleep. Therefore, the peptide fragment 208-240 is effective in inducing NREM sleep in a manner that is similar to the induction by the whole protein but without the induction of T cell proliferation.

TABLE 2

Effect of IL1β synthetic peptides on $PGE_2$ production by fibroblasts and proliferation of T cells.

| Peptide | PgE2[a] | [$^3$H] Thymidine Incorporation[b] | |
|---|---|---|---|
| | | Murine Thymocytes | Murine D10 Cells |
| 117-134 | — | — | 661 (33) |
| 178-207 | 13 (2) | 954 (86) | — |
| 299-228 | — | — | 2799 (652) |
| 208-240 | 105 (18) | 107 (16) | — |
| 247-269 | — | — | 3179 (50) |
| PBS[c] | BDL | 102 (10) | 478 (47) |

[a]$PGE_2$ levels measured after 48 h exposures of adherent RA cells in serum-free in MEM; values are one mean, with standard deviation in ( ), in ng/ml; BDL is below detection limit of 10 ng/ml.
[b]In counts per minute, with standard deviation in ( ).
[c]Physiologically Buffered Saline used as a control.

TABLE 3

Effects of hu-rIL1β and fragments on rabbit sleep and body temperature

| Substrate | Dose | N | NREMS[b] | REMS[b] | Colonic Temperature[a] | |
|---|---|---|---|---|---|---|
| | | | | | Start | End |
| aCSF | — | 8 | 45.4 (1.9) | 8.9 (1.0) | 39.1 (0.1) | 39.6 (0.1) |
| IL1β | 5 ng | 8 | 53.3 (3.2)* | 4.4 (0.8)* | 39.2 (0.0) | 40.0 (0.1)* |
| IL1β | 20 ng | 8 | 61.5 (4.3)* | 2.1 (0.6)* | 39.3 (0.1) | 41.0 (0.3)* |
| aCSF | — | 4 | 50.7 (1.8) | 11.9 (2.2) | 39.4 (0.1) | 39.5 ((.1) |
| 117-134 | 5 μg | 4 | 53.4 (3.1) | 9.2 (0.8) | 39.2 (0.1) | 39.7 (0.1) |
| aCSF | — | 4 | 52.3 (2.4) | 9.9 (1.6) | 39.2 (0.1) | 39.3 (0.1) |
| 117-134 | 10 μg | 4 | 48.9 (0.4) | 8.6 (2.2) | 39.3 (0.1) | 39.5 (0.1) |
| aCSF | — | 7 | 40.4 (1.8) | 5.9 (0.5) | 39.2 (0.1) | 39.3 (0.1) |
| 178-207 | 5 μg | 7 | 40.5 (2.5) | 7.7 (1.1) | 39.1 (0.1) | 39.5 (0.2) |
| aCSF | — | 4 | 55.0 (1.1) | 11.0 (0.5) | 39.2 (0.1) | 39.5 (0.0) |
| 178-207 | 25 μg | 4 | 53.8 (1.9) | 10.8 (0.9) | 39.4 (0.1) | 39.6 (0.0) |
| aCSF | — | 6 | 51.6 (2.6) | 10.2 (1.1) | 39.2 (0.1) | 39.3 (0.1) |
| 199-228 | 25 μg | 6 | 50.9 (3.9) | 20.0 (1.2) | 39.3 (0.1) | 39.4 (0.1) |
| aCSF | — | 9 | 48.1 (2.0) | 8.5 (0.7) | 39.2 (0.1) | 39.3 (0.1) |
| 208-240 | 25 μg | 9 | 58.8 (3.9)* | 5.8 (1.2) | 39.1 (0.1) | 40.0 (0.2)* |
| aCSF | — | 4 | 46.9 (2.8) | 9.2 (1.3) | 39.2 (0.1) | 39.4 (0.1) |
| 247-269 | 1 μg | 4 | 45.6 (1.9) | 9.3 (1.6) | 39.4 (0.1) | 39.7 (0.1) |
| aCSF | — | 3 | 44.8 (3.2) | 8.2 (1.3) | 39.4 (0.0) | 39.5 (0.1) |
| 247-269 | 5 μg | 3 | 46.5 (2.3) | 9.8 (1.8) | 39.4 (0.1) | 39.7 (0.1) |
| aCSF | — | 3 | 45.0 (2.4) | 8.1 (0.7) | 39.3 (0.0) | 39.4 (0.1) |
| 247-269 | 10 μg | 3 | 47.7 (2.3) | 7.9 (0.8) | 39.2 (0.1) | 39.5 (0.1) |

*Indicates significant difference between controls (aCSF) and peptides.
[a]in °C.
[b]percent of time over a six-hour recording period.

As may be seen from the foregoing, the present invention provides a protein fragment which will induce NREM sleep in a manner that is similar to the induction of NREM sleep induced by the whole protein IL1β.

Various of the features of the invention which are believed to be new are set forth in the appended claims.

What is claimed is:

1. A protein fragment for inducing sleep in mammals comprising a fragment of interleukin-1β from about amino acid 208 to about amino acid 240 and physiologically active analogs of said amino acids.

2. The protein fragment of claim 1 comprising the amino acid sequence:

Lys—Lys—Lys—Met—Glu—Lys—Arg—Phe—Val—
-210
Phe—Asn—Lys—Ile—Glu—Ile—Asn—Asn—Lys—
-220
Leu—Glu—Phe—Glu—Ser—Ala—Gln—Phe—Pro—
-230
Asn—Trp—Tyr—Ile—Ser—Thr,
-240 and physiologically active analogs of said amino acids.

3. The protein fragment of claim 2 further comprising a cysteine residue attached to thr$_{240}$.

4. The protein fragment of claim 1 derived by synthetic methods.

5. A method for inducing NREM sleep in mammals including humans comprising administering to the mammal a physiologically effective amount of a fragment of interleukin-1β, comprising from about amino acid 208 to about amino acid 240 and physiologically active analogs of said amino acids.

6. The method of claim 5 wherein the physiologically effective amount of said fragment is between about 5 μg/kg and about 25 μg/kg.

7. The method of claim 5 wherein said fragment comprises the amino acid sequence:

Lys—Lys—Lys—Met—Glu—Lys—Arg—Phe—Val—
-210
Phe—Asn—Lys—Ile—Glu—Ile—Asn—Asn—Lys—
-220
Leu—Glu—Phe—Glu—Ser—Ala—Gln—Phe—Pro—
-230
Asn—Trp—Tyr—Ile—Ser—Thr,
-240 and physiologically active analogs of said amino acids.

8. A pharmaceutical composition capable of inducing sleep in mammals comprising a physiologically acceptable carrier and the protein fragment of claim 1.

9. A pharmaceutical composition capable of inducing sleep in mammals comprising a physiologically acceptable carrier and the protein fragment of claim 2.

10. A pharmaceutical composition capable of inducing sleep in mammals comprising a physiologically acceptable carrier and the protein fragment of claim 3.

* * * * *